US008841085B2

(12) United States Patent
Kwon et al.

(10) Patent No.: US 8,841,085 B2
(45) Date of Patent: Sep. 23, 2014

(54) NANOPARTICLE SENSOR FOR MEASURING PROTEASE ACTIVITY AND METHOD FOR MANUFACTURING THE SAME

(75) Inventors: Ick-Chan Kwon, Seoul (KR); Kui-Won Choi, Seoul (KR); Kwang-Meyung Kim, Seoul (KR); In-Chan Youn, Seoul (KR); Seul-Ki Lee, Seoul (KR); Kyeong-Soon Park, Junranam-Do (KR); Dae-Hyuk Moon, Seoul (KR); Dae-Yoon Chi, Seoul (KR); Seung-Jin Lee, Seoul (KR); Seung-Jae Myung, Seoul (KR)

(73) Assignees: Korea Institute of Science and Technology (KR); The Asan Foundation (KR); Futurechem Co., Ltd. (KR)

( * ) Notice: Subject to any disclaimer, the term of this patent is extended or adjusted under 35 U.S.C. 154(b) by 578 days.

(21) Appl. No.: 13/060,902

(22) PCT Filed: Aug. 27, 2009

(86) PCT No.: PCT/KR2009/004794
§ 371 (c)(1),
(2), (4) Date: May 20, 2011

(87) PCT Pub. No.: WO2010/024609
PCT Pub. Date: Mar. 4, 2010

(65) Prior Publication Data
US 2011/0213121 A1   Sep. 1, 2011

(30) Foreign Application Priority Data

Aug. 29, 2008   (KR) ......................... 10-2008-0085497

(51) Int. Cl.
*C12Q 1/34*   (2006.01)
*C12Q 1/37*   (2006.01)
*G01N 33/543*   (2006.01)
*C12Q 1/04*   (2006.01)
*C12Q 1/06*   (2006.01)

(52) U.S. Cl.
CPC ............ *C12Q 1/37* (2013.01); *G01N 33/54346* (2013.01); *Y10S 977/773* (2013.01); *Y10S 977/774* (2013.01); *Y10S 977/807* (2013.01); *Y10S 977/811* (2013.01); *Y10S 977/953* (2013.01)
USPC .................. 435/23; 424/9.6; 435/18; 435/24; 435/34; 435/39; 977/773; 977/774; 977/807; 977/811; 977/953

(58) Field of Classification Search
USPC ..................... 424/9.6; 435/18, 23, 24, 34, 39; 977/773, 774, 807, 811, 953
See application file for complete search history.

(56) References Cited

U.S. PATENT DOCUMENTS 8,323,622 B2 *   12/2012   Kwon et al. ................... 424/9.6

OTHER PUBLICATIONS

Boeneman et al. 2009. Sensing Caspase 3 Activity with Quantum Dot-Fluorescent Protein Assemblies. Journal of American Chemical Society, vol. 131, pp. 3828-3829, Published on Web Feb. 25, 2009.*
Chang et al. 2005. Protease-activated quantum dot probes. Biochemical and Biophysical Research Communications, vol. 334, pp. 1317-1321.*
Xia et al. 2008. Multiplex Detection of Protease Activity with Quantum Dot Nanosensors Prepared by Intein-Mediated Specific Bioconjugation. Analytical Biochemistry, vol. 80, pp. 8649-8655.*
Medintz et al.2006. Proteolytic activity monitored by fluorescence resonance energy transfer through quantum-dot-peptide conjugates. Nature Materials, vol. 5, pp. 581-589.*
Kim et al (2006. Cell-Permeable and Biocompatible Polymeric Nanoparticles for Apoptosis Imaging. Journal of the American Chemical Society, vol. 128, pp. 3490-3491.*
Lee et al. 2008. Dark Quenched Matrix Metalloproteinase Fluorogenic Probe for Imaging Osteoarthritis Development in Vivo. Bioconjugate Chemistry, vol. 19, No. 9, pp. 1743-1747.*
Weilbaecher et al. 2005. Surface Immobilization of Peptides on SiO2 Nanobeads for a Protease Biosensor. IEEE-Xplore Nov. 2005, pp. 436-439.*
Tang et al. 2007. Preparation of Chitosan Nanoparticles as Carrier for Immobilized Enzyme. Applied Biochemistry and Biotechnology, vol. 136, pp. 77-96.*

* cited by examiner

*Primary Examiner* — Ralph Gitomer
*Assistant Examiner* — Kailash C Srivastava
(74) *Attorney, Agent, or Firm* — Ostrolenk Faber LLP (57) ABSTRACT

Disclosed are a nanoparticle sensor for measuring protease activity, for protease imaging, and a method for preparing the same. More specifically, the present invention relates to a nanoparticle sensor for measuring protease activity in which a fluorophore- and a quencher-conjugated peptide substrate is conjugated to a biocompatible polymer nanoparticle. The peptide substrate is specifically lysed by a protease. The sensor according to the present invention is capable of inhibiting emission of fluorescence with high extinctive activity of the quencher on a fluorescent material. But strong fluorescence is specifically emitted only if the peptide substrate is lysed by a specific protease. Therefore, the sensor is especially useful as a method for screening a novel drug such as a protease overexpression inhibitor, and early diagnosis of incurable diseases and various diseases such as autoimmune diseases including cancer, osteoarthritis, rheumatoid arthritis and dementia.

8 Claims, 6 Drawing Sheets

glycol chitosan     cholanic acid     glycol chitosan-dile acid (b)

FIG. 8

```
                        SEQUENCE LISTING

<160> NUMBER OF SEQ ID NOS: 13

<210> SEQ ID NO 1
<211> LENGTH: 10
<212> TYPE: PRT
<213> ORGANISM: Homo Sapiens

<400> SEQUENCE: 1

Gly Pro Leu Gly Val Arg Gly Lys Gly Gly
1               5                   10

<210> SEQ ID NO 2
<211> LENGTH: 12
<212> TYPE: PRT
<213> ORGANISM: Homo Sapiens

<400> SEQUENCE: 2

Gly Val Pro Leu Ser Leu Thr Met Gly Lys Gly Gly
1               5                   10

<210> SEQ ID NO 3
<211> LENGTH: 12
<212> TYPE: PRT
<213> ORGANISM: Homo Sapiens

<400> SEQUENCE: 3

Gly Pro Leu Gly Met Arg Gly Leu Gly Lys Gly Gly
1               5                   10

<210> SEQ ID NO 4
<211> LENGTH: 5
<212> TYPE: PRT
<213> ORGANISM: Homo Sapiens

<400> SEQUENCE: 4

Pro Leu Gly Leu Pro
1               5

<210> SEQ ID NO 5
<211> LENGTH: 7
<212> TYPE: PRT
<213> ORGANISM: Homo sapiens

<400> SEQUENCE: 5

Val Pro Leu Ser Leu Thr Met
1               5

<210> SEQ ID NO 6
<211> LENGTH: 6
<212> TYPE: PRT
<213> ORGANISM: Homo sapiens
```

```
<400> SEQUENCE: 6

Pro Leu Gly Met Arg Gly
1               5

<210> SEQ ID NO 7
<211> LENGTH: 7
<212> TYPE: PRT
<213> ORGANISM: Homo sapiens

<400> SEQUENCE: 7

Pro Ile Cys Phe Phe Arg Leu
1               5

<210> SEQ ID NO 8
<211> LENGTH: 5
<212> TYPE: PRT
<213> ORGANISM: Homo sapiens

<400> SEQUENCE: 8

His Ser Ser Leu Gln
1               5

<210> SEQ ID NO 9
<211> LENGTH: 4
<212> TYPE: PRT
<213> ORGANISM: Homo sapiens

<400> SEQUENCE: 9

Trp Glu His Asp
1

<210> SEQ ID NO 10
<211> LENGTH: 4
<212> TYPE: PRT
<213> ORGANISM: Homo sapiens

<400> SEQUENCE: 10

Asp Glu Val Asp
1

<210> SEQ ID NO 11
<211> LENGTH: 6
<212> TYPE: PRT
<213> ORGANISM: Homo sapiens

<400> SEQUENCE: 11

Asn Gln Glu Gln Val Ser
1               5

<210> SEQ ID NO 12
<211> LENGTH: 4
<212> TYPE: PRT
<213> ORGANISM: Homo sapiens

<400> SEQUENCE: 12

Gly Pro Gly Pro
1

<210> SEQ ID NO 13
<211> LENGTH: 10
<212> TYPE: PRT
<213> ORGANISM: Homo sapiens

<400> SEQUENCE: 13
```

```
Gly Val Ser Gln Asn Tyr Pro Ile Val Gly
1               5                   10
```

NANOPARTICLE SENSOR FOR MEASURING PROTEASE ACTIVITY AND METHOD FOR MANUFACTURING THE SAME

CROSS-REFERENCE TO RELATED APPLICATIONS

The present application is a 35 U.S.C. §§371 national phase conversion of PCT/KR2009/004794, filed Aug. 27, 2009, which claims priority of Korean Patent Application No. 10-2008-0085497, filed Aug. 29, 2008. The PCT International Application was published in the Korean language.

SEQUENCE LISTING

The instant application contains a Sequence Listing which has been submitted in ASCII format via EFS-Web and is hereby incorporated by reference in its entirety. Said ASCII copy, created on Feb. 25, 2014 is named 01560257.txt and is 2,269 bytes in size.

FIELD OF THE INVENTION

This specification relates to a nanoparticle sensor for measuring protease activity for protease imaging and a method for manufacturing the same.

BACKGROUND OF THE INVENTION

Most of cells in human bodies consist of proteins. Most of them are generated in an inactive state and specifically activated because numerous proteases may badly affect cells. That is, the proteases control activities or lives of proteins through hydrolysis of irreversible peptide bond. Examples of such control may include assigning positions of proteins inside or outside cells or separating them from cell surfaces, activating or deactivating various growth factors, hormones, cytokines, enzymes and proteases, converting agonists into antagonists and the like.

Proteases serve to control various cell functions in a broad sense. Since such control is derived by lysing bioactive substances, the functions and roles of the proteases are very important for living of every life. For example, serious results may be caused by shortage or overexpression of a specific protease, which may result in cancer, arthritis, neurodegenerative disorder, cardiovascular disease, autoimmune disease and the like. Hence, pharmaceutical companies have concentrated on development of novel drugs based on the proteases and its matrix proteins.

Active researches are in process to investigate functions of the proteases in cells and in human bodies based on such various functions of the proteases and the recently completed genome projects. According to the human genome projects, more than 500 protease-related genes have been discovered of human genes. In recent years, it has been newly found that the proteases are pivotally associated with various human diseases, such as cancer and dementia, and also cause such diseases. For example, matrix metalloproteases (MMPs) have been recognized as factors of lysing extracellular matrix in cells and bodies. However, it has been clarified through various studies that the MMPs have a connection to an integrin signaling transfer and a cell movement responsive to lysing of pericellular matrix. It has also been discovered that the MMPs play an important role in growth of cancer, such as Angiogenesis, invasion of cancer cells, transfer of cancer cells and the like. Cell apoptosis plays a core role in a biological process based on outbreak and cure of various diseases, and also plays a pivotal role in immune systems and removal of defective cells. If the cell apoptosis does not normally is work or is damaged by pathogenic organ, the result may be fatal, and developed into incurable diseases such as cancer, Alzheimer's disease, AIDS and the like. Consequently, development of novel drugs, targeting MMPs and caspase playing a pivotal role in the cell apoptosis, are in progress around various giant pharmaceutical companies.

As new matrix proteins are found, physiological functions of various protease groups may be newly inquired, thus to be expected to find target proteins for new drugs. However, any technology for quantitatively imaging and analyzing activities and expressions of specific proteases or non-invasively imaging expression level of proteases in vivo has not been introduced. Thus, development of related techniques is urgently needed.

Several methods for detecting (measuring) proteases have been currently used. A representative thereof may include 2-D gel and multi-stage liquid chromatography, the enzyme-linked immunosorbent assay (ELISA), a method for measuring a peak shift level using a spectroscopy by conjugating (binding) a fluorophore (fluorescent substance, fluorescent material) to a peptide substrate, which is specifically lysed by proteases, or the like. However, such methods need multi-stage measurement protocols, and thus are inefficient in economical and temporal aspects in use for screening a lot of drugs, such as developing novel drugs. Furthermore, those methods are configured to detect expression of a specific protease in the body or quantitatively analyzing the expression level of the specific protease, thereby being impossible to be used for early diagnosis of diseases.

To overcome such problems, a method for detecting proteases using a molecular imaging has been developed.

The most representative technology is to use a polymer sensor for protease imaging, developed in the Harvard medical school in 2001. The sensor is configured by a chemical binding of fluorophore-peptide substrate-biocompatible polymer, which is able to be lysed by proteases. When near-infrared ray fluorophores are present close to each other within a short distance (several tens of nm), emission of the fluorophore and excitation spectra are shared. Fluorescence of the fluorophore is thusly quenched by a florescence resonance energy transfer (FRET) principle. Accordingly, when the fluorophore-peptide is connected (conjugated, bound) to polymer, fluorescence is in a quenched (non-fluorescent) state due to the physical bonding between fluorophores. Then, when the distance between fluorophores is farther due to the peptide being lysed by protease, the fluorescence is recovered such that the sensor can image an expression level of the protease. What is important in an optical imaging technology is a signal-to-noise (S/N) ratio. If high fluorescence is contained in a background, an image resolution in a target biomolecule or biologic tissue cannot help being lowered. Thus, the quenching of the fluorescence is very important. Also, if fluorescence, which has been undetected due to being quenched, is emitted from a desired biomolecule or disease portion, high S/N ratio may be exhibited, thereby obtaining a clear image. The research has exhibited the quenching of the sensor by using a self-quenching that fluorescence is quenched when near-infrared fluorophores are present close to each other. However, the self-quenching based on the FRET is performed when the fluorophores are within a very short distance therebetween and does not exhibit superior fluorescence quenching rate.

To solve the problem, various quenchers are used. Among various quenchers, a black hole quencher as a complete absorber or the like has various absorption wavelengths. As one example, BHQ-1 very efficiently absorbs fluorescence emitted at wavelengths of 480-580 nm, BHQ-2 at 550-650 nm and BHQ-3 at 620-730 nm. For a single molecule of fluorophore-peptide substrate-quencher, fluorescence is recovered when the peptide substrate is lysed by protease to allow measuring of a quantity of protease and exhibiting of a higher fluorescence quenching rate than the self-quenching of the fluorophore-fluorophore binding (conjugate, bonding). However, the fluorophore-peptide substrate-quencher may be applied only to an in vitro kit, which analyzes a quantitative amount of the protease within a mixture due to instability and cell impermeability in vivo as peptide-specific properties. In addition, the single molecule of fluorophore-peptide substrate-quencher is difficult to emit high fluorescence, capable of being imaged only in vivo, which may result in difficulty of a real-time measurement of protein expression in vivo.

SUMMARY OF THE INVENTION

Therefore, an aspect of the detailed description is to provide a nanoparticle sensor for measuring activity of a protease for selectively imaging proteases expressed in cells and tissues in human bodies, the sensor in which a fluorophore, a peptide substrate specifically lysed by the protease, and a quencher for absorbing fluorescence of the fluorophore are connected (conjugated, bound) to a biocompatible polymer nanoparticle, and a method for manufacturing the same.

Another aspect of the detailed description is to provide a composition for is diagnosis of cancer, cerebral apoplexy and autoimmune disease or a composition for quantitative analysis of protease, the composition containing the nanoparticle sensor as a significant component.

To achieve these and other advantages and in accordance with the purpose of this specification, as embodied and broadly described herein, there is provided a nanoparticle sensor for measuring protease activity, the sensor in which a biocompatible polymer nanoparticle is conjugated (bound, connected) to a peptide substrate, which has a fluorophore and a quencher both bound thereto and is specifically lysed by protease.

The nanoparticle sensor for measuring protease activity may have the following structural formula 1:

[Structural Formula 1]

where A denotes a fluorophore, B denotes a peptide substrate specifically lysed by protease, C denotes a quencher, which absorbs fluorescence emitted from the fluorophore to exhibit a quenching effect, and D denotes a nanoparticle composed of a biocompatible polymer, which is specifically accumulated on cancer or an inflamed portion.

According to one detailed example, a carboxylic acid or -Sh group of cysteine present at C-terminal of the peptide substrate may be conjugated to the biocompatible polymer nanoparticle.

According to one detailed example, the peptide substrate may be a peptide bond to which the fluorophore and the quencher are conjugated.

According to one detailed example, the biocompatible polymer nanoparticle may consist of a biocompatible polymer selected from a group consisting of chitosan, dextran, hyaluronic acid, polyamino acid and heparin, and a nanoparticle conjugated with a hydrophobic material selected from a group consisting of bile acid, fatty acid and cholesterol.

According to one detailed example, the protease may be one selected from a group consisting of matrix metalloproteinases (MMPs), thrombin, factor xiiia (FXIIIa), caspase, urokinase plasminogen activator (uPA), HIV protease, dipeptidyl peptidase (DPP-IV) and proteasome.

According to one detailed example, the fluorophore may be one emitting red or near-infrared fluorescence. The fluorophore may be one selected from a group consisting of cyanine, fluorescein, tetramethylrhodamine, alexa, bodipy and derivatives thereof.

According to one detailed example, the peptide may be a peptide substrate, which is specifically lysed by protease.

According to one detailed example, the quencher may be selected from a group including a black hole quencher, a blackberry quencher and derivatives thereof, which are able to quench fluorescence.

According to one detailed example, the protease may be MMP, A may be Cy5.5, B may be a peptide substrate specifically lysed by the MMP, C may be BHQ-3, and D may be a chitosan nanoparticle.

As another aspect, this specification provides a composition, which has the nanoparticle sensor for measuring protease activity as a significant component and is capable of screening drugs for inhibit overexpression of proteases or efficacies of the drugs.

As another aspect, this specification may provide a method for fabricating the nanoparticle sensor for measuring protease activity. The method may include:

(a) reacting a near-infrared fluorophore with a peptide substrate, specific to a particular protease, to conjugate (bond, bind) them to each other;

(b) conjugating a quencher to the peptide substrate; and (c) conjugating a polymer nanoparticle to the fluorophore-peptide substrate-quencher to manufacture a nanoparticle sensor for measuring protease activity.

As another aspect, this specification may provide a composition for cancer diagnosis, which contains the nanoparticle sensor for measuring the protease activity as a significant component, and is capable of diagnosing a cancer selected from a group including squamous cell carcinoma, uterine cancer, uterine cervical cancer, prostatic cancer, head and neck cancer, pancreas cancer, brain tumor, breast cancer, liver cancer, skin cancer, esophageal cancer, testicular cancer, kidney cancer, large intestine cancer, rectal cancer, gastric cancer, bladder cancer, ovarian cancer, cholangiocarcinoma and cholangiocarcinoma.

As another aspect, this specification may provide a composition for diagnosis of autoimmune diseases, containing the nanoparticle sensor for measuring the protease activity as a significant component.

According to one detailed example, the autoimmune diseases may be inflammatory diseases, which may include osteoarthritis or rheumatoid arthritis.

As another aspect, this specification may provide a composition for quantitative analysis of proteases, which are expressed in cells and tissues, the composition containing the nanoparticle sensor for measuring the protease activity as a significant component.

Effect

As mentioned above, according to a nanoparticle sensor for measuring a protease activity, in which a fluorophore, a peptide substrate specifically lysed by protease, and a quencher capable of absorbing fluorescence emitted from the fluoro- phore are conjugated (bound) with a biocompatible polymer nanoparticle, the sensor is capable of inhibiting emission of fluorescence with high extinctive activity of the quencher on a fluorescent material. But strong fluorescence is specifically emitted only if the peptide substrate is lysed by a specific protease. Therefore, the sensor is especially useful for a method for screening a novel drug such as a protease overexpression inhibitor, and early diagnosis of incurable diseases and various diseases such as autoimmune diseases including cancer, osteoarthritis, rheumatoid arthritis and dementia.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

DETAILED DESCRIPTION OF THE INVENTION

To achieve those aspects, this specification provides a nanoparticle sensor for measuring protease activity, capable of specifically reacting with various proteases and allowing fluorescence emission only to a target protease, by conjugating a fluorophore and a quencher to a certain peptide substrate, which is specifically lysed by a protease expressed in a cell and in vivo so as to maximize a quenching rate of fluorescence and conjugating this to a biocompatible, cell-permeable polymer nanoparticle.

More especially, the nanoparticle sensor for measuring the protease activity may have, but not limited to, the following structural formula 1 and be a nanoparticle sensor for measuring an activity of protease expressed in a cell or a biological tissue.

[Structural Formula 1]

where A denotes a fluorophore, B denotes a peptide substrate specifically lysed by protease, C denotes a quencher, which absorbs fluorescence emitted from the fluorophore to exhibit a quenching effect, and D denotes a nanoparticle composed of a biocompatible polymer, which is specifically accumulated on cancer or an inflamed portion.

Here, as a detailed example, the nanoparticle may be conjugated to a carboxylic acid or -Sh group of cysteine present at C-terminal of the peptide substrate.

Here, the fluorophore and the quencher may be conjugated to any portion of the peptide substrate, at which they can form a peptide bond with the peptide substrate, for example, conjugated to amino-terminal, lysine, cysteine or carboxylic acid.

The protease may be one selected from a group consisting of matrix metalloproteinases (MMPs), thrombin, factor xiiia (FXIIIa), caspase, urokinase plasminogen activator (uPA), HIV protease, dipeptidyl peptidase (DPP-IV) and proteasome.

The peptide substrate C may be a peptide substrate specifically lysed by proteases, for example, a peptide targeted by MMP, thrombin, caspase, which becomes active during cell apoptosis process, proteasome and the like. A peptide substrate to be used may vary depending on a type of protease.

The following table 1 shows peptide substrate sequences for various proteases. However, the peptide substrate used in the nanoparticle sensor according to this specification may not be limited to the specific peptide sequences.

TABLE 1

| Disease | Protease | Peptide Substrate/lysed site |
|---|---|---|
| Cancer | MMP-2/9 | PLG/LP (SEQ ID NO: 4) |
|  | MMP-7 | VPLS/LTM (SEQ ID NO: 5) |
| Atherosclerosis | MMP-13 | PLG/MRG (SEQ ID NO: 6) |
| Rheumatoid | Cathepsins B | K/K |
|  | Cathepsins D | PICF/FRL (SEQ ID NO: 7) |
| Arthritis | PSA | HSSLQ/ (SEQ ID NO: 8) |
| Apoptosis | Capspase-1 | WEHD/ (SEQ ID NO: 9) |
|  | Capspase-3 | DEVD/ (SEQ ID NO: 10) |
| Cardiovascular | Thrombin | F(Pin)R/S |
|  | Fijian | NQ/EQVS (SEQ ID NO: 11) |
| Diabetes | DPP-IV | GP/GP (SEQ ID NO: 12) |
| HIV protease | HSV | GVSQNY/PIVG (SEQ ID NO: 13) |

As shown in Table 1, proteases, which play a pivotal role in various diseases, have been already reported and also many peptide substrates, which are specifically lysed by those proteases, have also been reported. In addition to the peptide substrates shown in Table 1, peptide substrates lysed by various enzymes are disclosed in the Sigma-Aldrich Corporation web site (see http://www.sigmaaldrich.com/catalog/search/TablePage/14573356), and also various proteases can be detected using those peptide substrates.

The fluorophore A may be a fluorophore capable of emitting visible or near-infrared fluorescence. Examples of the fluorophore may include fluorescein, bodipy, tetramethylrhodamine, alexa, cyanine, allopicocyanine, fluorophores that emits other fluorescence, or derivatives thereof. Also, fluorophores having high quantum yield may be preferred. Among others, cyanine and alexa fluorophores may be especially preferred because they emit and absorb near-infrared rays thus to minimize interference with or absorption into cells, bloods, and living tissues, etc.

The quencher C, which is chemically conjugated to the fluorophore-bound peptide substrate, may generate a strong (high) quenching effect by absorbing light having the wavelength emitted from the fluorophore, such that fluorescence cannot be emitted when the peptide is not lysed by a specific protease. Such quenching effect may be exhibited when a distance between the fluorophore and the quenching is within several nanometers (nm). In other words, when the peptide substrate is lysed by reaction with a specific protease, the fluorophore and the quencher conjugated to the peptide are separated farther away from each other and the quenching effect is thusly disappeared. Accordingly, specific fluorescence of the fluorophore can be emitted, thereby allowing qualitative and quantitative analysis of protease.

The quencher may absorb light having the wavelength emitted from the fluorophore to maximize a quenching effect. The quenching effect can be maximized only when using a quencher having the same or almost similar wavelength as or to that of fluorescence emitted from a fluorophore. Thus, the type of quencher used may vary according to the range of wavelengths emitted from fluorophores.

The quencher used in the present invention is 'dark quencher' capable of quenching fluorescence emitted from the fluorophore not by emitting out absorbed excited fluorescence energy. The commercially available quenchers may include black hole quenchers (BHQ, WO01/86001, Biosearch Technologies Inc. Novato, Calif., USA), blackberry quenchers (BBQ, BERRY&ASSOCIATES Inc. Dexter, Mi, USA), etc.

The nanoparticles D may have uniform sizes of 50-500 nm in an aqueous state. The nanoparticle may be formed by conjugating a hydrophobic compound to a biocompatible polymer, such as chitosan, poly(ethylene imine), poly(amino acid), etc. having a molecular weight of 1,000 to 1,000,000 Da.

As used herein, the term "biocompatibility" indicates capability which does not cause toxic responses, inflammatory responses, immune responses, carcinogenic possibilities and the like, is atoxic or harmless to living bodies without causing immunological rejections, and is compatible with living tissues or living systems with high affinity. Also, the biocompatible polymers may include chitosan, dextran, hyaluronic acid, polyamino acid, heparin and the like, and hydrophilic chitosan polymers may be preferred. Any kind of chitosan having a molecular weight of 103 to 106, especially, a water-soluble chitosan as a natural polymer with high biocompatibility, more preferably, a glycol chitosan having enhanced water-solubility by virtue of introduction of glycol group may be used.

Examples of the hydrophilic materials conjugated to the biocompatible polymers may include bile acid, fatty acid and cholesterol.

As one especial example, in regard of a nanoparticle sensor for measuring protease activity, the peptide B may be a peptide substrate, which is specifically lysed by various proteases over-expressed in cancerous and inflammatory portions, the fluorophore A may be Cy5.5 as a cyanine fluorophore, which is conjugated to an amino terminal of the peptide to exhibit near-infrared fluorescence, the quencher C may be a black hole quencher-3 (BBQ-3), which is conjugated to lysine or cysteine of the peptide to absorb fluorescence emitted from the fluorophore so as to maximize a quenching effect. Also, the nanoparticle D may be chemically conjugated to a carboxylic acid or -Sh group of cysteine present at C-terminal of the peptide so as to function as a carrier to specifically deliver fluorophore A-B-C in a non-fluorescent state to cancerous and inflammatory portions.

In addition, since the nanoparticle sensor is formed based upon polymer nanoparticles, it is cell-permeable and able to be specifically accumulated on tissues having inflammatory diseases including cancerous tissues in vivo by an enhanced permeability retention (EPR) effect, which thusly allows non-invasive measurement and imaging of expression level of proteases, which are specifically expressed in cells and in vivo disease regions.

The nanoparticle sensor for measuring the protease activity, for protease imaging, may be manufactured by conjugating a fluorophore and a quencher to a peptide substrate, which is specifically lysed by a specific protease, and conjugating the peptide substrate to a polymer nanoparticle.

In more detail, a method for fabricating the polymer nanoparticle sensor for protease imaging may include (a) reacting a near-infrared fluorophore with a peptide substrate, which is specific to a particular protease, (b) conjugating (binding) a quencher to the peptide substrate, and (c) conjugating a polymer nanoparticle to the fluorophore-peptide substrate-quencher, which is in a non-fluorescent state, to manufacture a nanoparticle sensor for measuring protease activity.

The method may, if necessary, further include refining or analyzing the fluorophore-peptide substrate-quencher-nanoparticle sensor manufactured by the method.

In one detailed example, the peptide substrate may be appropriately synthesized, and the synthesis may use various peptide synthesis methods, well-known to those skilled in the art, for example, Fmoc strategy according to a solid phase synthesis and the like.

Also, a protective group present at an N-terminal or middle portion of the synthesized peptide may be removed to react with a fluorophore or derivative thereof, which can be conjugated to a functional group located at the protective group-removed portion (probably the N-terminal or the middle portion of the peptide), thus to be conjugated to each other. Afterwards, a protective group present at another portion (probably the N-terminal or the middle portion), from which the proactive group is not removed, may be removed to react with a fluorophore or a derivative thereof, which can be conjugated to a functional group present at the another protective group-removed portion, thus to be conjugated to each other.

For conjugating the conjugated fluorophore-peptide substrate-quencher to the biocompatible polymer nanoparticle, the biocompatible polymer may be chemically conjugated using a hydrophilic biopolymer and a hydrophobic material, thereby forming nanoparticles having uniform sizes in an aqueous state.

A distance between the fluorophore A and the quencher C may be controlled to minimize fluorescence of the fluorophore by way of maximizing a quenching effect between the fluorophore and the quencher.

The fluorophore and the quencher may be preferably synthesized to minimize fluorescence intensity by a quenching effect, which is generated by maintaining the distance between the fluorophore and the quencher within several nanometers. Also, the fluorophore-peptide-quencher-nanoparticle derivative, as the nanoparticle sensor for detecting the protease activity, can facilitate variation and control of the fluorophore, the quencher and the peptide substrate, thus to easily control a sensor for a desired protease and various sensors having desired wavelengths, thereby allowing design of sensors for various proteases.

Therefore, activity and inhibition of proteases can fast be screened through imaging, the nanoparticle sensor can be applied to a drug screening, a real-time imaging in cells and tissues and a non-invasive tissue imaging. In detail, the nanoparticle sensor may easily detect existence, activity, inhibition and the like of a protease, which is present within a specific tissue or cell in vivo, thereby being used for various purposes such as cell imaging, specific tissue imaging, drug carrier and the like.

Also, the nanoparticle sensor for measuring the protease activity may be used for a method for imaging proteases in cancers including squamous cell carcinoma, uterine cancer, uterine cervical cancer, prostatic cancer, head and neck cancer, pancreas cancer, brain tumor, breast cancer, liver cancer, skin cancer, esophageal cancer, testicular cancer, kidney cancer, large intestine cancer, rectal cancer, gastric cancer, bladder cancer, ovarian cancer, cholangiocarcinoma, cholangiocarcinoma and the like, and inflammatory diseases such as osteoarthritis, rheumatoid arthritis and the like. As one example, the sensor for imaging the proteases may be used when imaging proteases in incurable diseases including dementia, cerebral apoplexy and the like.

As one example, this specification provides a composition for diagnosis of a cancer selected from a group consisting of squamous cell carcinoma, uterine cancer, uterine cervical cancer, prostatic cancer, head and neck cancer, pancreas cancer, brain tumor, breast cancer, liver cancer, skin cancer, esophageal cancer, testicular cancer, kidney cancer, large intestine cancer, rectal cancer, gastric cancer, bladder cancer, ovarian cancer, cholangiocarcinoma and cholangiocarcinoma, a composition for diagnosis of dementia or cerebral apoplexy, or a composition for diagnosis of autoimmune diseases, in detail, inflammatory diseases including osteoarthritis or rheumatoid arthritis. Such composition may contain (have) the nanoparticle for measuring the protease activity as a significant component.

Also, as an application of the nanoparticle sensor for measuring the protease activity, the composition may be a composition for quantitative analysis of proteases expressed in cells and tissues or a composition for screening drugs inhibiting overexpression of proteases or efficacies of drugs. The composition may contain the nanoparticle sensor for measuring the protease activity as a significant component.

In addition, the composition may be applicable both to in vivo and in vitro, and useful in various fields such as high-throughput screening required for development of novel drugs, early diagnosis and the like.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

Hereinafter, the examples of this specification will be described in more detail. Here, the following examples are merely illustrative and should not be construed as limiting the claims of the present disclosure.

Example 1

Preparation of Fluorophore-Peptide-Quencher-Nanoparticle Derivative 1-1. Preparation of Fluorophore-Peptide-Quenching Derivative First, to prepare a fluorophore- and quencher-conjugated peptide, the peptide was prepared by Fmoc strategy according to a solid phase synthesis, and the fluorophore and the quencher were chemically conjugated to the prepared peptide sequence.

As the fluorophores, Cy5.5 (ex/em, 670/690), TRITC (ex/em, 547/572) and FITC (ex/em, 490/520) were used. As the quenchers for quenching fluorescence emitted from each of Cy5.5, TRITC and FITC fluorophores, BHQ-3 (abs. 620 nm-730 nm), BHQ-2 (abs. 550 nm-650 nm) and BHQ-1 (abs. 480 nm-580 nm) (Biosearch Technologies Inc.) were used, respectively.

Figure 1:
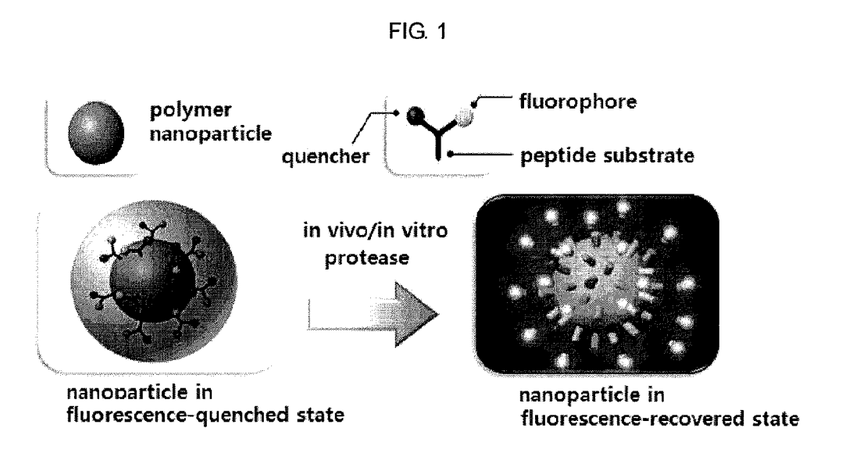
FIG. 1 is a diagram of a sensor for measuring protease activity, which is composed of a peptide, a near-infrared fluorophore, a quencher and a polymer nanoparticle, and capable of recovering strong fluorescence and allowing protease imaging when peptide is specifically lysed by a protease from a quenched state.
Figure 2:
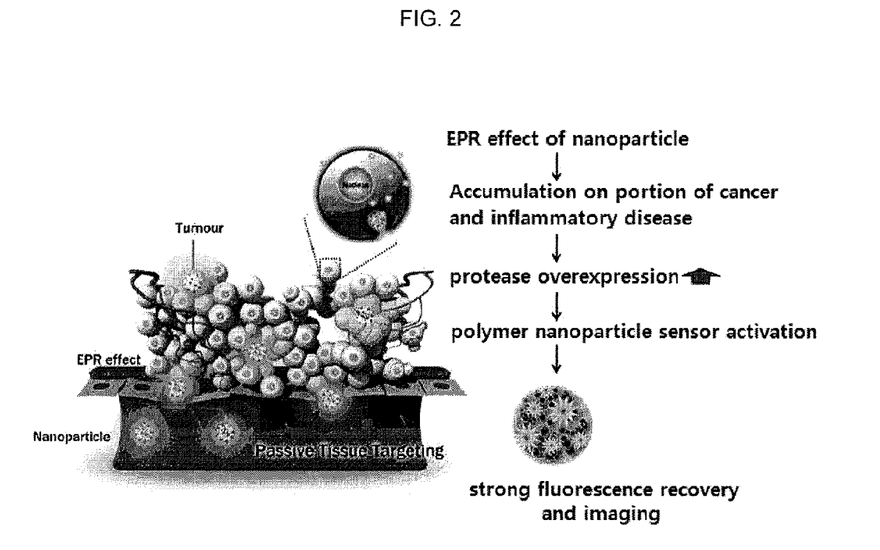
FIG. 2 is a mimetic diagram showing a principle that the protease activity measuring sensor based on polymer nanoparticles are specifically accumulated on an inflammatory portion such that strong fluorescence is restored by various proteases, which are overexpressed in disease portions.
Figure 3:
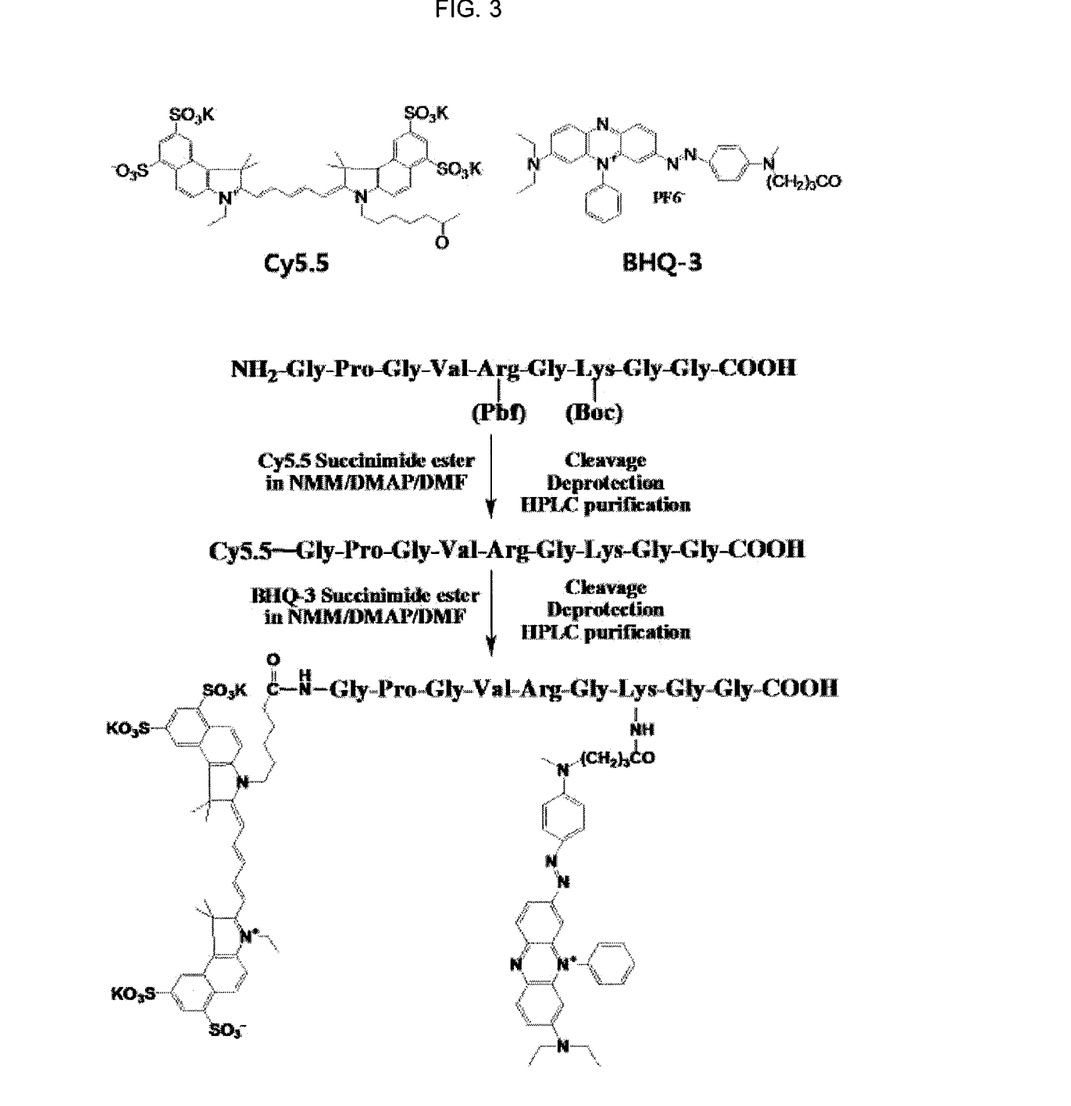
FIG. 3 is a diagram showing an exemplary synthesis of P1 composed of fluorophore-peptide-quencher.

As one example, a process of synthesizing a fluorophore-peptide-quencher, which emitted fluorescence by being selectively lysed by MMP-2, was as follows (see FIG. 3).

NH2-Gly-Pro-Leu-Gly-Val-Arg(Pbf)-Gly-Lys(Boc)-Gly-Gly-COOH (SEQ ID NO: 1) as a peptide substrate, selectively lysed by proteases such as MMPs, was prepared by the Fmoc peptide synthesis. 5 mg of the peptide substrate was mixed with a solution, in which 8.5 mg of Cy5.5-HNS ester, 8 μl of N-methyl morpholin and 0.3 mg of 4-dimethylamino pyridine, which were all near-infrared fluorophores, were dissolved in 200 μl of dimethylformamide, and reacted with each other at room temperature for 12 hours. The completely reacted solution was precipitated in 4 ml of cold ethyl ether and centrifuged to remove a supernatant, followed by washing with 2 ml of cold ethyl ether. After removing the ethyl ether from a surface of the solution, the ethyl ether removed solution was dried in a speed vacuum or a vacuum oven, thereby preparing Cy5.5-Gly-Pro-Leu-Gly-Val-Arg(Pbf)-Gly-Lys(Boc)-Gly-Gly-COOH (SEQ ID NO: 1) precursor.

To remove a protective group of the dried peptide precursor, the precursor was put in a mixture containing 1 ml of trifluoroacetic acid, 25 μl of distilled water and 25 μl of anisole, and reacted with each other at room temperature for 1 hour. After completely removing the solution using a rotary pump, the resultant was dissolved in 1 ml of HPLC eluent (saline solution containing 0.1% TFA: acetonitrile containing 0.1% TFA=1:1) and then filtered (0.45 μm, an organic solvent filter). The HPLC was stabilized in 5% acetonitrile containing 0.1% TFA and 95% DDW containing 0.1% TFA, using HPLC eluent (DDW containing 0.1% TFA: acetonitrile containing 0.1% TFA=1:1) and agilent ZORBAX SB-C18 column (9.4×150 mm). Gradient elution (5% of acetonitrile (containing 0.1% TFA) at 0 minute, 22% at 5 minute and 40% at 20 minute vs DW (containing 0.1% TFA) was carried out for 20 minutes to isolate the product. Here, after measuring UV at 220 nm, and fluorescence (ex/em: 675/690 nm) using a fluorescence detector (FLD), Cy5.5-Gly-Pro-Leu-Gly-Val-Arg-Gly-Lys-Gly-Gly-COOH (SEQ ID NO: 1) product was isolated. A molecular weight of the isolated product was lyophilized after being imaged and analyzed by using a mass. 2 mg of the substance reacted with a mixture, in which 0.71 mg of BHQ3-NHS ester (Biosearch Technologies Inc.), 1.5 μl of NMM and 0.2 mg of DMAP were dissolved in 30 μl of DMSO, at room temperature for 12 hours. The HPLC was stabilized in 5% acetonitrile containing 0.1% TFA and 95% saline solution containing 0.1% TFA, using HPLC eluent (DDW containing 0.1% TFA: acetonitrile containing 0.1 TFA=1:1) and agilent ZORBAX SB-C18 column (9.4×150 mm). Gradient elution (5% of acetonitrile (containing 0.1% TFA) at 0 minute, 30% at 5 minute and 70% at 25 minute vs DDW (containing 0.1% TFA) was carried out for 25 minutes to isolate the product. Here, after measuring UV at 220 nm, and fluorescence (ex/em: 675/690 nm) using a fluorescence detector (FLD), Cy5.5-Gly-Pro-Leu-Gly-Val-Arg-Gly-Lys(BHQ3)-Gly-Gly-COOH (SEQ ID NO: 1) product was isolated. A molecular weight of the isolated product was lyophilized after being imaged and analyzed by using a mass. Such Cy5.5-Gly-Pro-Leu-Gly-Val-Arg-Gly-Lys(BHQ3)-Gly-Gly-COOH (SEQ ID NO: 1) product to which fluorophore and the quencher were conjugated, was named as P1. According to the above synthesis processes, various complexes having the following sequences were synthesized.

P1: Cy5.5-Gly-Pro-Leu-Gly-Val-Arg-Gly-Lys(BHQ3)-Gly-Gly-COOH (SEQ ID NO: 1)
P2: Cy5.5-Gly-Val-Pro-Leu-Ser-Leu-Thr-Met-Gly-Lys(BHQ3)-Gly-Gly-COOH (SEQ ID NO: 2)
P3: Cy5.5-Gly-Pro-Leu-Gly-Met-Arg-Gly-Leu-Gly-Lys(BHQ3)-Gly-Gly-COOH (SEQ ID NO: 3)

1-2. Preparation of Polymer Nanoparticle Derivative

Figure 4:
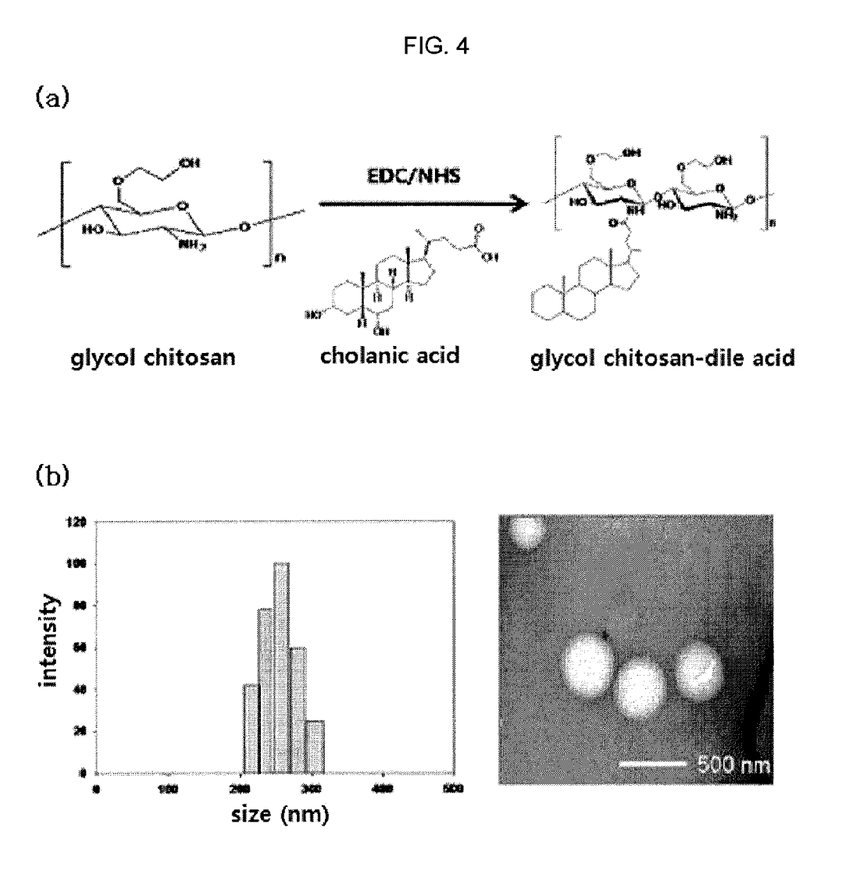
FIG. 4A is a mimetic diagram showing a synthesis of glycol chitosan-bile acid derivative capable of consisting of uniform nanoparticle in an aqueous state.
FIG. 4B is a particle size distribution view and TEM image showing that glycol chitosan-bile acid derivative forms uniform nanoparticles in an aqueous state.

To prepare a biocompatible polymer nanoparticle, which had a high selectivity with respect to cancers and inflammatory tissues by EPR effect and was cell-permeable, a biocompatible glycol chitosan (a molecular weight of 250,000 Da) was used as a polymer, and a cholanic acid as a type of bile acid was used as a hydrophobic material. The thusly-obtained substance was glycol chitosan-bile acid (see FIG. 4).

According to the processes shown in the reaction formula of FIG. 4A, 500 mg of glycol chitosan was dissolved in 60 Ml of distilled water and then diluted by pouring 90 Ml of MeOH therein. The solution was mixed with a mixture, in which a colinic acid, 1-ethyl-3-(3-dimethylaminopropyl) carbodiimid (EDC) and N-hydroxy succinimide (NHS) are dissolved in MeOH, and reacted at room temperature for 12 hours. After complete reaction, the solution was dialyzed sequentially in distilled water/MeOH (1:3) solution for 24 hours, distilled water/MeOH (1:1) for 24 hours and distilled water for 24 hours, followed by lyophilization. Consequently, as shown in FIG. 4B, polymer nanoparticles having a size of 250 nm in an aqueous state were prepared.

1-3. Preparation of Fluorophore-Peptide-Quencher-Polymer Nanoparticle Derivative The fluorophore-peptide-quencher prepared at process 1-1 was chemically conjugated to the polymer nanoparticle, thereby finally preparing a nanoparticle sensor for measuring protease activity based on the polymer nanoparticles.

In detail, P1, P2 and P3 of the fluorophore-peptide-quencher derivatives, prepared at process 1-1, were conjugated to glycol chitosan based nanoparticles.

10 mg of glycol chitosan-dile acid, synthesized at process 1-2, was poured in a tube and dissolved in 100 μl of DMSO. 14 Ml of PBS (pH 7.4) wad added into the solution and dispersed completely using sonicator, thereby forming nanoparticles. The fluorophore-peptide-quencher derivative (P1, P2 or P3) was dissolved in 100 μl of DMSO, mixed with 100 μl of PBS (pH 6.0), and then mixed with EDC (1 mg) and Sulfo-NHS (1 mg), thereby reacting with each other at room temperature for 15 minutes. After complete reaction, the solution was added into the glycol chitosan-dile acid solution to react with each other at room temperature for 12 hours. After complete reaction, the solution was dialyzed sequentially in distilled water/MeOH (1:3) solution for 24 hours, distilled water/MeOH (1:1) for 24 hours and distilled water for 24 hours, followed by lyophilization. The nanoparticles prepared using P1, P2 or P3 and the chitosan-dile acid according to the preparation method were named as PN1, PN2 and PN3.

Experimental Example 1

Variation of Optical Properties of Protease Sensor by MMP-Specific Lysing

Specific selectivities for proteases of the polymer based sensors, which was prepared in Example 1 and specific to MMPs, were observed. Each of the sensors (PN1, PN2 and PN3) was added in a mixture containing proteases, thereby measuring fluorescent intensities (FIs) recovered according to time.

In detail, PN1, PN2 and PN3 (10 μg/Ml each), which specifically reacted with MMPs to recover fluorescence, were added in MMP-2, MMP-3, MMP-7, MMP-9 or MMP-13 (1 μg/Ml) all in an active state, and emission of fluorescence by zymolysis was observed. For activating each MMP, the MMPs were added in TCNB solution (0.1 M of Tris, 5 mM of calcium chloride, 200 mM of NaCl and 0.1% of brij), in which p-aminophenyl mercuric acid were mixed, followed by reaction at 37° C. for 1 hour. The activated MMPs respectively reacted with a polymer nanoparticle based sensor in 200 μl of solution in a 96-well at 37° C., thereby observing fluorescence recovered levels through a fluorescence spectrometer.

It was exhibited that upon reacting the PN1 with each of MMP-2, MMP-3, MMP-7, MMP-9 and MMP-13 for 60 minutes, as shown in Table 2, fluorescent intensities (FIs) were recovered by 9.7, 2.0, 1, 9.2 and 12.3 times, respectively. Hence, it could be noticed that relatively high FIs were recovered by the reaction between the PN1 and MMP-2, MMP-3, MMP-9 and MMP-13.

TABLE 2

Fluorescence recovery properties of protease activity measuring sensor PN1 with respect to MMPs

| Time (min) | Variation of fluorescent intensity (FI) with respect Protease | | | | |
| --- | --- | --- | --- | --- | --- |
| | MMP-2 | MMP-3 | MMP-7 | MMP-9 | MMP-13 |
| 0 | 378.6 | 307.4 | 278.5 | 350.5 | 664.6 |
| 10 | 952.3 | 284.9 | 288.3 | 680.3 | 1933 |
| 20 | 1715 | 362.6 | 287.2 | 1350 | 3933 |
| 30 | 2387 | 421.3 | 290.1 | 2010 | 5292 |
| 40 | 2916 | 506.4 | 294.2 | 2248 | 6512 |
| 50 | 3210 | 537.3 | 299.6 | 2846 | 7608 |
| 60 | 3658 | 629.5 | 302.1 | 3221 | 8182 |

It was exhibited, as shown in Table 3, that upon reacting the PN2 with each of MMP-2, MMP-3, MMP-7, MMP-9 and MMP-13 for 60 minutes, FIs were recovered by 1.8, 3.6, 3.9, 1.3 and 4.8 times, respectively. Hence, it could be noticed that relatively high/FIs were recovered by the reaction between the PN2 and MMP-3, MMP-7 and MMP-13.

TABLE 3

Fluorescence recovery properties of protease activity measuring sensor PN2 with respect to MMPs

| Time (min) | Variation of fluorescent intensity (FI) with respect Protease | | | | |
|---|---|---|---|---|---|
| | MMP-2 | MMP-3 | MMP-7 | MMP-9 | MMP-13 |
| 0 | 271.1 | 336.1 | 327.9 | 182 | 286.7 |
| 10 | 245 | 225.7 | 653 | 186.3 | 723.5 |
| 20 | 350 | 407.8 | 992.8 | 186 | 1063 |
| 30 | 280.2 | 842.8 | 1161 | 187.1 | 1231 |
| 40 | 334.8 | 946 | 1252 | 239.4 | 1350 |
| 50 | 426.1 | 1073 | 1310 | 233.3 | 1361 |
| 60 | 493.5 | 1229 | 1276 | 247.9 | 1373 |

It was exhibited, as shown in Table 4, that upon reacting the PN3 with each of MMP-2, MMP-3, MMP-7, MMP-9 and MMP-13 for 60 minutes, FIs were recovered by 3.7, 2.4, 0.8, 1.3 and 4.3 times, respectively. Hence, it could be noticed that relatively high FIs were recovered by the reaction between the PN3 and MMP-2, MMP-3 and MMP-13.

TABLE 4

Fluorescence recovery properties of protease activity measuring sensor PN4 with respect to MMPs

| Time (min) | Variation of fluorescent intensity (FI) with respect Protease | | | | |
|---|---|---|---|---|---|
| | MMP-2 | MMP-3 | MMP-7 | MMP-9 | MMP-13 |
| 0 | 77.37 | 102.5 | 104.3 | 100.9 | 100.6 |
| 10 | 90.98 | 128.3 | 90.14 | 106.1 | 131.2 |
| 20 | 125.2 | 143.2 | 87.61 | 109.1 | 166.1 |
| 30 | 151.3 | 174.4 | 86.97 | 114.3 | 234.4 |
| 40 | 189.4 | 199.5 | 91.48 | 127.6 | 280.7 |
| 50 | 238.5 | 217.2 | 94.88 | 129.8 | 355.3 |
| 60 | 286.7 | 249.3 | 86.33 | 133.3 | 455.5 |

Example 2

Fluorescence Recovery and Imaging of Protease Activity Measuring Sensor According to Concentration of Protease The sensors prepared in Example 1 were used to quantitatively analyze concentrations of proteases. In detail, according to the same method as in Example 1, activated MMP-2s respectively in concentrations of 0, 0.55, 1, 3, 7 and 14 nmol/L were added in the PN1 sensor and reacted with each other at 37° C. for 60 minutes, thereby observing emission levels of fluorescence (fluorescent intensities) using a fluorescence spectrometer and a digital imaging system (Kodak Image Station 4000 mM).

Figure 5:
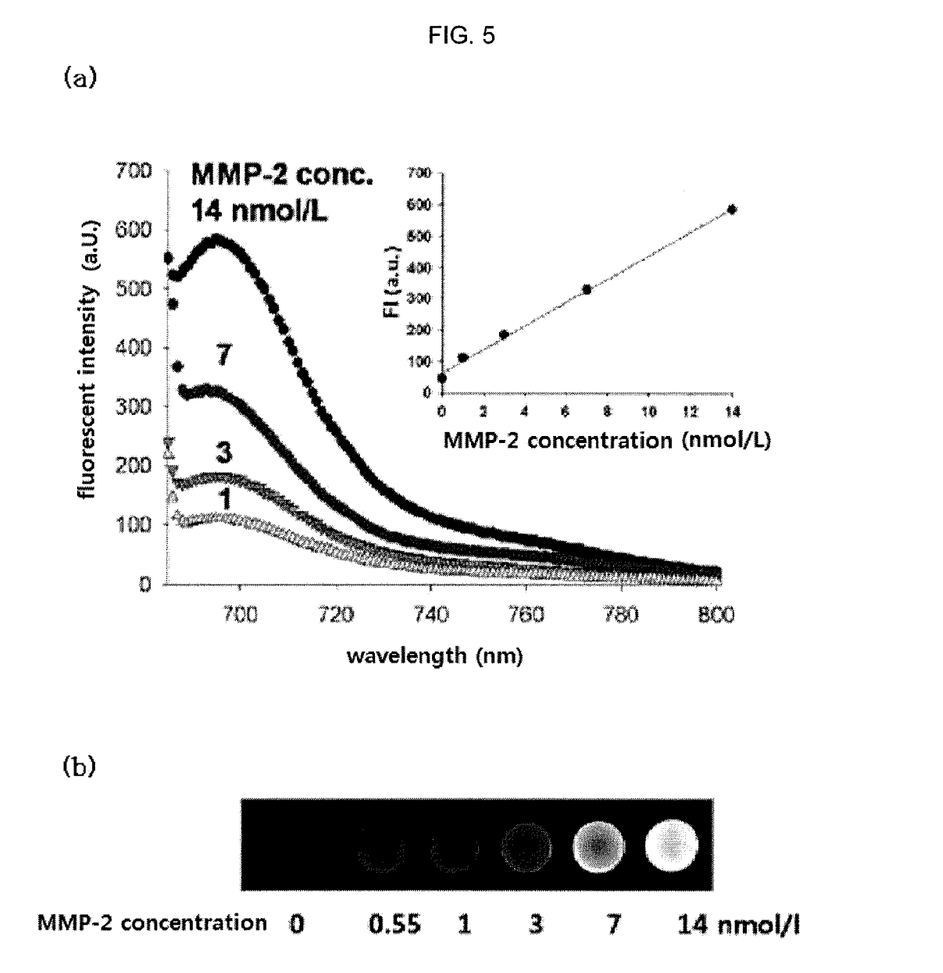
FIG. 5A is a diagram showing that fluorescent intensity constantly increases in response to an increase in concentration of a protease MMP-2 so as to allow quantitative analysis of the protease.
FIG. 5B is a diagram showing, through a fluorescence imaging system, that fluorescence intensity constantly increases in response to an increase in concentration of a protease MMP-2.

As shown in FIG. 5A, fluorescence emitted from the PN1 sensor was increased in proportion to the concentration of the added MMP-2 protease. It was thusly proved that a specific protease concentration within a specimen could be quantitatively detected by measuring the fluorescence intensity of an experimental group, and imaging thereof could be carried out using an optical imaging system (see FIG. 5B).

Experimental Example 3

MMP Expression in Animal Model Having Cancer and Cancer Cell Imaging Using Protease Activity Measuring Sensor Squamous cell carcinoma (SCC7) was subdermally implanted in C3H/HeN mouse to make an animal model having the cancer. When a cancer tissue was grown over 5 mm in size, PN1 was intravenously injected into the disease animal to evaluate possibility of imaging the cancer tissue through imaging of MMPs, which were expressed in the cancer tissue.

The squamous cell carcinoma (SCC7) has been known as a cancer cell expressing a large amount of MMP-2. Experiments were carried out with three animal experimental groups, namely, a normal mouse, a mouse having a cancer, into which PN1 (100 µl, 100 µg) was injected, and a mouse having a cancer, to which PN1 and MMP-2 expression inhibitor were simultaneously injected. An optical imaging was carried out by using Optix™ system.

Figure 6:
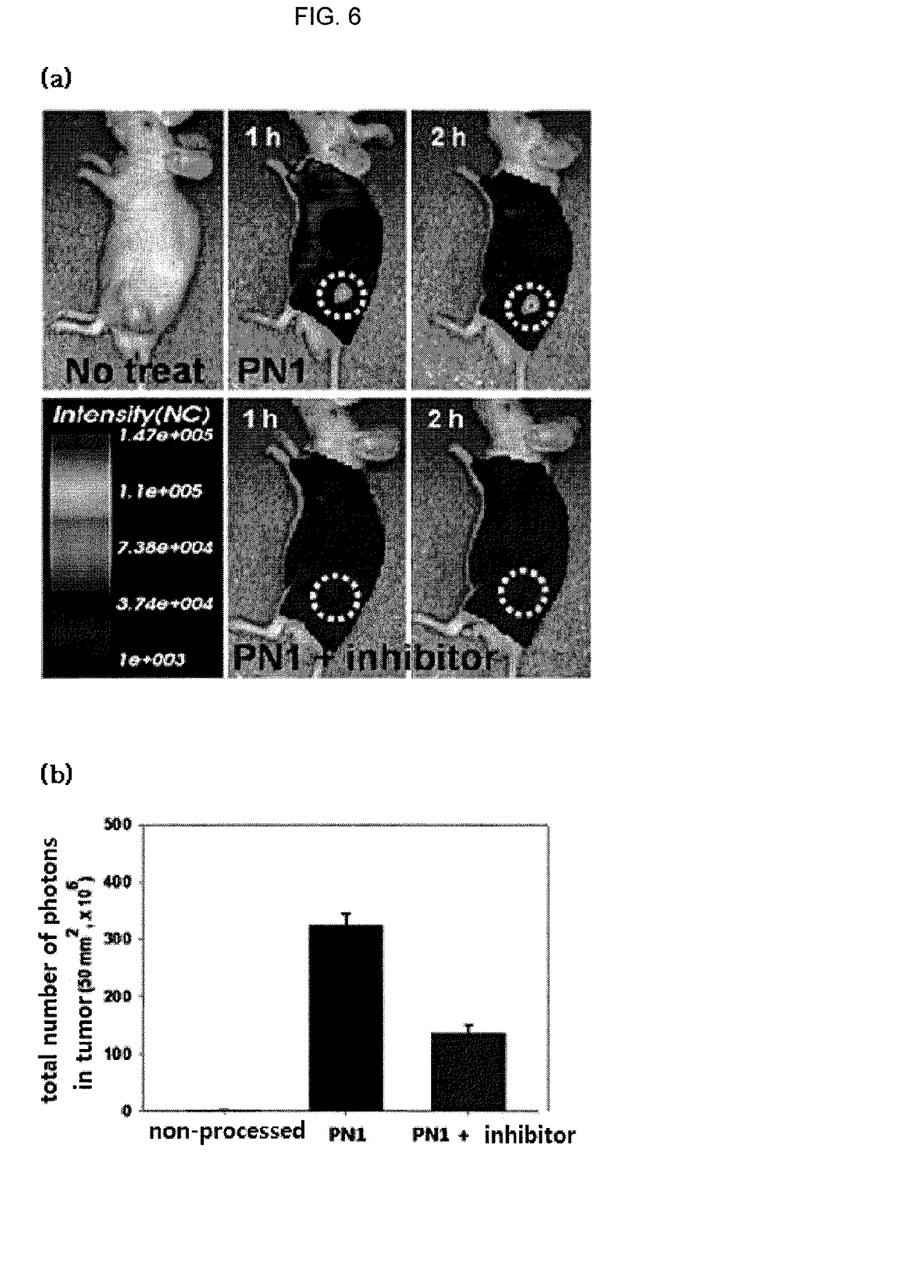
FIG. 6A is a diagram showing near-infrared images of a tissue taken from a normal animal model, and tissues taken respectively from a cancer-induced animal model having PN1 injected therein, and a cancer-induced animal model having PN1 injected therein and processed with MMP-2 inhibitor, after 1 hour and 2 hours, respectively, following such processing.
FIG. 6B is a graph numerically showing a fluorescent intensity of a tissue taken from a normal animal model, and fluorescent intensities of tissues taken respectively from a cancer-induced animal model having PN1 injected therein, and a cancer-induced animal model having PN1 injected therein and processed with MMP-2 inhibitor.

As a result, as shown in FIG. 6A, it could be observed that the sensor injected into the normal mouse (No treat) without cancer cells did not emit fluorescence but the mouse (PN1) having cancer cells emitted strong fluorescence as time elapsed. Also, a strong fluorescence recovery, which was exhibited in the MMP-2 expressed cancer cells, was not observed upon injecting the MMP-2 inhibitor for inhibiting the activity of the MMP-2 (PN1+inhibitor). As shown in FIG. 6B, the fluorescence recovery rate was observed as low as 2.2 times upon injecting the MMPs activity inhibitor, which meant that PN1 specifically reacted with the cancer cell overexpressing MMP-2 in vivo to exhibit strong fluorescence emitted. Consequently, it was proved that MMPs expressed levels in vivo and thusly-caused cancer cells can be specifically imaged.

Figure 7:
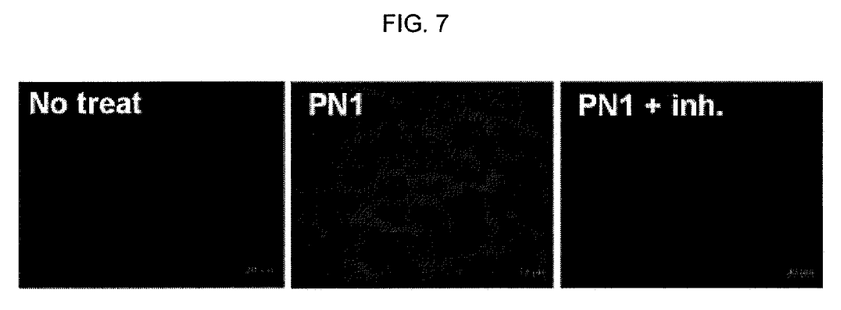
FIG. 7 shows microscopic images of a tissue taken from a normal animal model, and tissues taken respectively from a cancer-induced animal model having PN1 injected therein, and a cancer-induced animal model having PN1 injected therein and processed with MMP-2 inhibitor.

Also, a fluorescence recovery level of PN1 according to injection or non-injection of MMP-2 inhibitor into a cancer tissue, from which MMP-2 was overexpressed, was measured. After making animal experimental groups, namely, a normal mouse, a mouse having cancer cells, into which PN1 was intravenously injected, and a mouse having cancer cells, into which PN1 was intravenously injected and then MMP-2 inhibitor was injected according to the same method as in the above experimental example, tissues or cancer tissues were cut out from the mice, thereby observing fluorescent intensities specifically emitted from cancer cells by using a fluorescent microscope. Referring to FIG. 7, fluorescence was not recovered in the normal mouse, while strong fluorescence was emitted from the cancer tissues of the mice having the cancer cells. However, similar to the result of the animal test, the fluorescence recovery was inhibited in the cancer tissue processed by the MMP-2 inhibitor so as to exhibit extremely low fluorescence intensity.

Experimental Example 4

MMP Expression in Animal Model Having Osteoarthropathy and Imaging for Osteoarthritis Using Protease Activity Measuring Sensor MMPs are overexpressed in inflammatory diseases such as osteoarthritis and rheumatoid arthritis. Thus, it is possible to early diagnose arthritis through imaging such disease portions by using MMPs as markers. In general, it had been known that MMP-13 is overexpressed in a disease portion of osteoarthritis. Thus, we attempted an early diagnosis for the osteoarthritis through MMP-13 imaging in an animal model having the osteoarthritis by using the sensor prepared in Example 1.

After anesthetizing Sprague-Dawley mouse (250~300 g), a right knee joint was protruded and a sinew was cut out to make an animal model having an osteoarthritis. After 6 to 8 weeks, the PN3 sensor prepared in Example 1 was injected into a joint tissue to image MMP-13 expressed in the disease portion. In detail, PN3 (100 μl, 100 μg) was injected into a normal joint tissue and an osteoarthritis joint tissue, respectively, followed by observation using a digital imaging system (Kodak Image Station 4000 mM).

Figure 8:
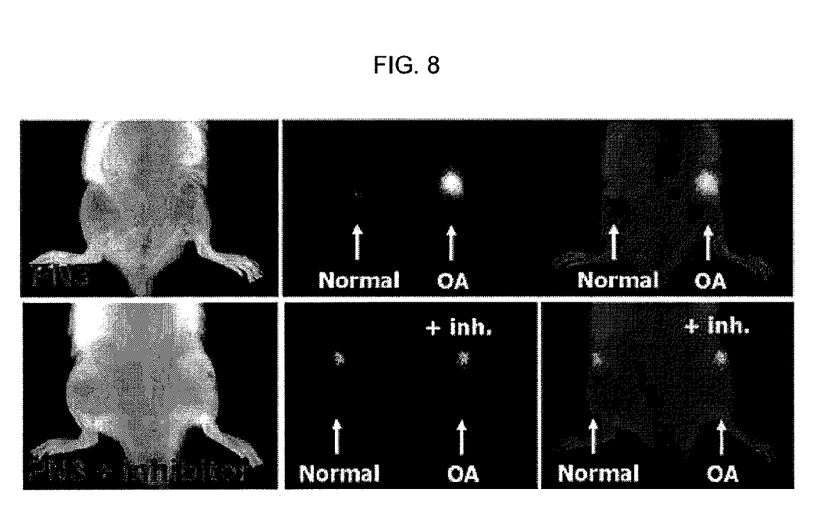
FIG. 8 is a diagram showing near-infrared images of a normal joint tissue, a joint tissue portion taken from an osteoarthritis-induced animal model having PN3 as a protease sensor injected therein, and a joint tissue portion taken from an osteoarthritis-induced animal model having PN3 as a protease sensor injected therein and processed with MMP-13 inhibitor, after 2 hours following such processing.

Referring to FIG. 8, it could be observed that the PN3 injected into the normal joint tissue (Normal) did not emitted fluorescence but the osteoarthritis joint tissue, in which MMP-13 was overexpressed, emitted strong fluorescence. Also, the strong fluorescence recovery, which was exhibited in the osteoarthritis portion having the MMP-13 overexpressed, was not observed upon injecting MMMP-13 inhibitor for inhibiting the activity of the MMP-13 (+inh). Therefore, it could be noticed that the PN3 exhibited the strong fluorescence emission in the osteoarthritis portion, in which MMP-13 was overexpressed in vivo. Finally, it was known that MMPs expressed levels in vivo and the thusly-caused inflammatory diseases can be specifically imaged.

What is claimed is:

1. A nanoparticle sensor for measuring protease activity, in which a fluorophore and a quencher are conjugated to a peptide substrate, and the peptide substrate is covalently conjugated to a biocompatible polymer nanoparticle, the peptide substrate being
specifically lysed by protease,
wherein the protease is selected from a group consisting of matrix metalloproteinases (MMPs); the peptide substrate is selected from a group consisting of Gly-Pro-Leu-Gly-Val-Arg-Gly-Lys-Gly-Gly (SEQ ID NO: 1), Gly-Val-Pro-Leu-Ser-Leu-Thr-Met-Gly-Lys-Gly-Gly (SEQ ID NO: 2) and Gly-Pro-Leu-Gly-Met-Arg-Gly-Leu-Gly-Lys-Gly-Gly (SEQ ID NO: 3); and the biocompatible polymer nanoparticle is a hydrophobic modified glycol chitosan.

2. The nanoparticle sensor of claim 1, wherein the nanoparticle sensor for measuring protease activity has the following structural formula 1:

[Structural Formula 1]

where A denotes a fluorophore, B denotes a peptide substrate specifically lysed by protease, C denotes a quencher, which absorbs fluorescence emitted from the fluorophore to exhibit a quenching effect, and D denotes a nanoparticle composed of a biocompatible polymer specifically accumulated on a cancer-present portion or an inflamed portion"

wherein the protease is selected from a group consisting of matrix metalloproteinases (MMPs); the peptide substrate is selected from a group consisting of Gly-Pro-Leu-Gly-Val-Arg-Gly-Lys-Gly-Gly (SEQ ID NO: 1), Gly-Val-Pro-Leu-Ser-Leu-Thr-Met-Gly-Lys-Gly-Gly (SEQ ID NO: 2) and Gly-Pro-Leu-Gly-Met-Arg-Gly-Leu-Gly-Lys-Gly-Gly (SEQ ID NO: 3); and biocompatible polymer nanoparticle is a hydrophobic modified glycol chitosan.

3. The nanoparticle sensor of claim 1, wherein the glycol chitosan is modified with at least one material selected from a group consisting of bile acid, fatty acid and cholesterol.

4. The nanoparticle sensor of claim 1, wherein the matrix metalloproteinases (MMPs) is selected from a group consisting of MMP-2, MMP-3, MMP-7, MMP-9 and MMP-13.

5. The nanoparticle sensor of claim 1, wherein the fluorophore emits red or near-infrared fluorescence.

6. The nanoparticle sensor of claim 1, wherein the quencher is selected from a group including a black hole quencher, a blackberry quencher and derivatives thereof, those being able to quench fluorescence.

7. The nanoparticle sensor of claim 1, wherein the protease is MMP-13, the fluorophore is Cy5.5, the peptide substrate is Gly-Pro-Leu-Gly-Val-Arg-Gly-Lys-Gly-Gly (SEO ID NO:1), the quencher is BHQ-3, and the biocompatible polymer nanoparticle is a bile acid modified glycol chitosan nanoparticle.

8. The nanoparticle sensor of claim 5, wherein the fluorophore is selected from a group consisting of cyanine, fluorescein, tetramethylrhodamine, alexa, bodipy and derivatives thereof.

* * * * *